(12) United States Patent
Burgoa Roman et al.

(10) Patent No.: US 9,171,360 B2
(45) Date of Patent: Oct. 27, 2015

(54) METHOD FOR DETERMINING THE LUMINANCE OF TRAFFIC SIGNS AND DEVICE FOR IMPLEMENTING SAME

(75) Inventors: Francisco Javier Burgoa Roman, Boecillo (ES); Jose Antonio Gutierrez Mendez, Boecillo (ES); Alberto Mansilla Gallo, Boecillo (ES); Diego Oritz de Lejarazu Machin, Boecillo (ES); Alberto Senen Perales Garcia, Boecillo (ES)

(73) Assignee: DBI/Cidaut Technologies, LLC, Hazelton, PA (US)

( * ) Notice: Subject to any disclaimer, the term of this patent is extended or adjusted under 35 U.S.C. 154(b) by 773 days.

(21) Appl. No.: 12/866,888

(22) PCT Filed: Apr. 8, 2008

(86) PCT No.: PCT/ES2008/000214
§ 371 (c)(1),
(2), (4) Date: Aug. 9, 2010

(87) PCT Pub. No.: WO2009/101219
PCT Pub. Date: Aug. 20, 2009

(65) Prior Publication Data
US 2010/0316252 A1    Dec. 16, 2010

(30) Foreign Application Priority Data
Feb. 12, 2008   (ES) .................... 200800371

(51) Int. Cl.
*G06K 9/00* (2006.01)
*G06T 5/50* (2006.01)
(Continued)

(52) U.S. Cl.
CPC . *G06T 5/50* (2013.01); *B60Q 1/085* (2013.01); *B60Q 1/18* (2013.01); *G01N 21/55* (2013.01); *B60Q 2300/314* (2013.01); *B60Q 2300/45* (2013.01); *G01N 2021/551* (2013.01)

(58) Field of Classification Search
CPC . G01N 21/55; G01N 2021/551; B60Q 1/085; B60Q 2300/45; B60Q 1/18; B60Q 2300/314; B60Q 1/2603; B60Q 2300/103; B60R 21/01538; G06T 5/50
USPC ................ 382/100, 103, 104, 190, 274, 275; 348/148
See application file for complete search history.

(56) References Cited
U.S. PATENT DOCUMENTS

| 4,553,848 A | 11/1985 | Rosicke et al. |
|---|---|---|
| 6,266,442 B1 | 7/2001 | Laumeyer et al. |

(Continued)

FOREIGN PATENT DOCUMENTS

| EP | 1486799 | 12/2004 |
|---|---|---|
| EP | 1486799 A2 * | 12/2004 |

(Continued)

OTHER PUBLICATIONS

International Search Report, mailing date Oct. 28, 2008, for corresponding International Application No. PCT/ES2008/000214.
(Continued)

*Primary Examiner* — Kim Vu
*Assistant Examiner* — Michael Vanchy, Jr.
(74) *Attorney, Agent, or Firm* — Morgan Lewis & Bockius LLP

(57) ABSTRACT

The method of the invention comprises: obtaining a sequence of at least two images, with different levels of illumination; extracting the region containing the sign in the image; calculating the luminance values of the signs; and obtaining the difference in luminance of the sign corresponding to the two levels of illumination. The value obtained is the luminance of the sign (11) corresponding to an illumination equal to the difference between the illuminations, or additional illumination. This result is based on the additive property of luminance, according to which the luminance of a sign is the sum of the luminance produced by each source of illumination. A basic illumination device (5), an additional illumination device (7), at least one camera for taking images, and image recording, positioning and synchronism systems are required to implement the method.

9 Claims, 2 Drawing Sheets

(51) Int. Cl.
  *B60Q 1/08*   (2006.01)
  *B60Q 1/18*   (2006.01)
  *G01N 21/55*  (2014.01)

(56) References Cited

U.S. PATENT DOCUMENTS

| | | | |
|---|---|---|---|
| 6,674,878 | B2 | 1/2004 | Retterath et al. |
| 6,810,135 | B1* | 10/2004 | Berenz et al. ............ 382/118 |
| 6,891,960 | B2 | 5/2005 | Retterath et al. |
| 7,043,057 | B2 | 5/2006 | Retterath et al. |
| 7,173,707 | B2 | 2/2007 | Retterath et al. |
| 7,298,487 | B2 | 11/2007 | Hansen et al. |
| 7,411,681 | B2 | 8/2008 | Retterath et al. |
| 7,515,736 | B2 | 4/2009 | Retterath et al. |
| 7,995,796 | B2 | 8/2011 | Retterath et al. |
| 2002/0176605 | A1* | 11/2002 | Stafsudd et al. ............ 382/106 |
| 2004/0062442 | A1* | 4/2004 | Laumeyer et al. ........... 382/190 |
| 2005/0146725 | A1 | 7/2005 | Hansen et al. |
| 2006/0238714 | A1* | 10/2006 | Fox et al. ................... 352/49 |
| 2007/0216904 | A1 | 9/2007 | Retterath et al. |
| 2007/0262765 | A1* | 11/2007 | Joos et al. .................. 323/299 |
| 2009/0078870 | A1* | 3/2009 | Haruna ....................... 250/330 |
| 2010/0316252 | A1 | 12/2010 | Roman et al. |
| 2012/0065940 | A1 | 3/2012 | Retterath et al. |
| 2013/0271613 | A1 | 10/2013 | Retterath et al. |

FOREIGN PATENT DOCUMENTS

| | | |
|---|---|---|
| EP | 1580074 A1 | 9/2005 |
| EP | 1976296 | 1/2008 |
| FR | 2661248 | 10/1991 |
| JP | 2000353292 | 12/2000 |
| JP | 2000149195 A | 5/2005 |
| JP | 2008015970 A | 1/2008 |
| TW | 242637 B | 11/2005 |
| WO | WO 2007/083741 | 7/2007 |

OTHER PUBLICATIONS

Written Opinion of the International Preliminary Examining Authority, mailing date Jul. 6, 2010, for corresponding International Application No. PCT/ES2008/000214.

European Patent Application No. 08761461, Supplementary European Search Report and Opinion, dated May 23, 2011, 7 pages.

European Patent Application No. 08761461, Response to European Search Report and Opinion, dated Oct. 20, 2011, 13 pages.

European Patent Application No. 08761461, Response to Communication Pursuant to 161 (2) and 162 EP, dated Oct. 19, 2010, 6 pages.

European Patent Application No. 08761461, Supplementary European Search Report and Opinion, dated Jun. 1, 2011, 7 pages.

European Patent Application No. 08761461, Corrected Form 1703, dated Oct. 11, 2011, 6 pages.

European Patent Application No. 08761461., Response to European Search Report and Opinion, dated Oct. 20, 2011, 13 pages.

European Patent Application No. 08761461, Communication Pursuant to Article 94(3) EPC, dated Dec. 18, 2012, 6 pages.

European Patent Application No. 08761461, Response to Communication Pursuant to Article 94(3) EPC, dated Mar. 26, 2013, 14 pages.

\* cited by examiner

METHOD FOR DETERMINING THE LUMINANCE OF TRAFFIC SIGNS AND DEVICE FOR IMPLEMENTING SAME

The present invention relates to a procedure and device permitting the luminance provided by a sign installed on the road to be calculated, isolating the existing ambient illumination conditions. The calculation of the luminance is carried out on the basis of analysing the images gathered by an image recording system, and is applied to all signs appearing in those images.

The present invention encompasses the calculation of the luminance both of signs consisting of back-reflecting material and those that are internally lit, and to any traffic sign in general.

The invention comprises a set of lights and a procedure permitting the elimination of any effects which external illumination could have on the measurement, whether these come from other road users or from ambient illumination, along with a control system for the illumination provided by the vehicle. The illumination system used by the invention complies with existing standards in terms of illumination systems fitted to vehicles, the intensity is not high and it is not disturbing to road users, and the tests can be conducted without interrupting the traffic.

The invention comprises a moving system for the synchronized recording of images and data, referenced by means of a positioning system and an automatic system for sign identification and processing.

BACKGROUND OF THE INVENTION

The evaluation of the state of traffic signs installed on the road has normally been done by means of analysing two parameters:
  The back-reflection coefficient: Property of back-reflecting materials, which permits light to be returned in the same direction as the incident light.
  The luminance: Quantity of light returned by the sign to which the eye is sensitive.

The back-reflection coefficient is a parameter characteristic of the material, whose value falls off as the sign deteriorates. In order to evaluate it, systems have been developed such as those described in documents U.S. Pat. No. 7,173,707, U.S. Pat. No. 7,043,057 and U.S. Pat. No. 6,674,878, in which procedures are described for measuring the multiple back-reflection values or three-dimensional map of back-reflection coefficients provided by the sign. This measurement is made via a system that is capable of providing illumination by means of a high intensity stroboscopic light and which measures the different values of light intensity. It then generates some surfaces of back-reflection coefficients and simulates the back-reflection values along the road, recreating a virtual drive.

But, although the back-reflection coefficient or the three-dimensional map of back-reflection coefficients is a characteristic parameter of the sign, in order to obtain the luminance value (the parameter that really defines the visibility conditions) indirect methods have to be applied in which theoretical models of the illumination are used. The stated documents therefore lead to the problem of how to make a direct measurement of the luminance without having to be subject to intermediate operations based on unreal theoretical models.

Another problem that is raised by using the back-reflection coefficient lies in the fact that it is only applicable to back-reflecting signs, and signs that are internally lit have to be discarded from the analysis.

To make a direct calculation of the luminance (in units of $cd/m^2$) there exist various apparatus known as luminance meters. In order to make a measurement of the magnitude, these devices require certain specific conditions of stability and illumination, and the measurement they provide is of a point source. This equipment therefore displays serious drawbacks for making a simultaneous measurement while moving of all the signs lying within the analysis zone. The luminance measurements would have to be made one at a time, and in different zones of the sign, in order to then obtain an average of them.

Moreover, as the measurement requires a strictly controlled type of illumination, we would have to discard data that is influenced by the effects of moving traffic, external lighting, etc.

As a consequence, it is an objective of the present invention to have a procedure and a device that would permit the luminance of the sign to be determined:
  Directly, making a direct measurement of the physical parameter.
  Automatically, for all signs appearing in a scene.
  While circulating with a vehicle.
  On the basis of a known or standardized light source, independently of the existence of other external light sources at the moment of the measurement.
  Independently of whether the sign is back-reflecting, or internally lit, or any other kind of traffic sign.
  Independently of the level of back-reflection which this type of sign provides once installed on the road.

DESCRIPTION OF THE INVENTION

The present invention comprises a procedure and device for calculating the luminance provided by traffic signs arranged along the road, the measurement being based on certain light sources whose illumination conditions are known and controlled in turns of form and intensity. To achieve this, the images picked up by a mobile data gathering system are used. The procedure permits the interferences produced by uncontrolled external illuminations to be cancelled out, obtaining the luminance in the zones that are sought. The internal oscillations of the vehicle affecting its own illumination are also cancelled out. The invention permits simultaneous analysis of all the signs appearing in the images gathered by the moving vehicle, and is applied both to the back-reflecting type and to internally lit signs or to any other kind of traffic sign.

The present invention provides a series of improvements over existing systems by permitting a direct calculation to be made of the luminance from a moving vehicle, without any need to use theoretical models of illumination. It isolates the measurement from the interferences produced by light sources other than those of the vehicle. It also allows measurements to be carried out safely, without any need to cut off the traffic, since it does not use high intensity lamps and the measurements can be made at the usual road speed.

The visibility of a vertical road sign is directly related to the luminance provided by that sign. Luminance is defined as the ratio of luminous intensity of the surface apparently seen by the eye in a defined direction. Its unit is $cd/m^2$.

With the procedure described in the present invention, a measurement is made of the luminance using at least one digital camera, irrespective of whether it is colour or black and white, duly calibrated, in such a way that the luminous energy in the form of photons received by each pixel of the camera sensor is reflected as the luminance of a section of material. The camera or cameras to be used can be digital, analogue or any other kind, with their corresponding accessories for carrying out those operations.

In order to obtain the luminance level of each pixel in the image starting from a colour or black and white camera, it is necessary to perform two transformations. First of all, in the case of colour cameras, each level of red, blue and green of the pixel is combined with some appropriate weightings, specified in standard CIE-121, in order to convert it to a grey level. Secondly, it is transformed directly to luminance starting from a change equation obtained by comparison with a laboratory luminance meter.

With the method described, by using at least one digital camera it is possible to cover several signs simultaneously if they appear in the image. The images are processed in such a way that each sign is automatically identified and the luminance values are obtained for each of them.

The light intensity provided for the sign, whether this be from the actual vehicle itself or from other sources in the environs, has a direct influence on the measurement of the luminance of the back-reflecting materials. For the correct measurement, an illumination has been considered that eliminates the variability owing to the internal oscillations of the vehicle (of voltage, for example).

Moreover, in order to cancel out the perturbations produced by external light sources, a calculation technique of the luminance is proposed based on a differentiation of the values starting from at least two different illumination levels.

In some types of vertical signs, the luminance is provided by an internally generated illumination. On the other hand, in others it depends on the light provided by an external illumination and which is returned by the vertical sign, as occurs in the case of back-reflecting materials. The procedure and device proposed here are applicable to any traffic sign.

The procedure of the present invention for calculating the luminance comprises the following stages:
  Obtaining a sequence of images composed of at least two images with different illumination levels.
  Extracting the region where the sign is on the image.
  Calculating the luminance values of the signs.
  Obtaining the luminance difference of the sign corresponding to the two illumination levels.

The value obtained is the luminance of the sign corresponding to an illumination equal to the difference in the illuminations, or additional illumination. This result is based on the additive property of luminance, according to which the luminance calculated for each sign is the sum of the luminances produced by each light source.

In one of the images, the luminance is the sum of that due to the base illumination $L_a$, that due to the additional illumination $L_b$ and the uncontrolled ambient illumination $L_c$ (other vehicles, public lighting, etc). So the measured luminance is $$L1 = L_a + L_b + L_c,$$

Analogously, for the other image, the luminance will be due to the base illumination base $L_a$ and the ambient illumination $L_d$. The measured luminance will be:

$$L2 = L_a + L_d.$$

As the synchronism system ensures that the difference between the images to process is minimum in terms of the ambient illumination, we can assume that:

$$L_c = L_d.$$

If we deduct one level from the other, we obtain the value of the differential luminance corresponding to the additional illumination.

$$\Delta L = L1 - L2 = L_b$$

In this way a luminance value is obtained that is based on some lamps whose illumination conditions are known and controlled in terms of form and intensity, and which is independent of other uncontrolled external light sources.

In order to carry out the procedure of the invention, a device is used which, fitted to a vehicle, comprises:
  At least one camera for capturing the images.
  A base illumination device.
  An additional illumination device.
  A positioning system.
  A system for image and data recording and treatment.
  A synchronism system.

Among the advantages presented by the invention we can point out:
  It is not based on point source measurements, like those that can be provided by back-reflectometers or luminance meters.
  The analysis is carried out automatically for all the signs appearing in a scene.
  The measurements are taken by means of a moving vehicle.
  The measurement is made for a light source whose photometry is known and its level of light intensity is controlled.
  The measurement is not affected by the existence of other eternal light sources, ambient or similar.
  It permits an analysis of its state of visibility, independently of the level of back-reflection that the sign provides once installed on the road.
  It functions independently of whether the sign is back-reflecting or internally lit, or any other kind.

BRIEF DESCRIPTION OF THE DRAWINGS

To complement the foregoing description, and with the aim of aiding a better understanding of the characteristics of the invention, a detailed description of a preferred embodiment is going to be made, on the basis of a set of plans accompanying this descriptive specification in which, on an orientative rather than limiting basis, the following has been represented.

FIG. 3 shows the vehicle with the base illumination and additional illumination switched on.

FIG. 4 shows the vehicle with just the base illumination switched on.

In the above figures, the numerical references correspond to the following parts and elements.
  1. Driver.
  2. Sign panel.
  3. Distance between the driver and the sign.
  4. Normal to the sign panel 2.
  5. Base illumination.
  6. Stabilizer for the base illumination.
  7. Additional Illumination.
  8. Adjustment and control of the additional illumination.
  9. Light intensity sensor.
  10. Public lighting.
  11. Vertical traffic sign.

DETAILED DESCRIPTION OF A PREFERRED EMBODIMENT

Figure 1:
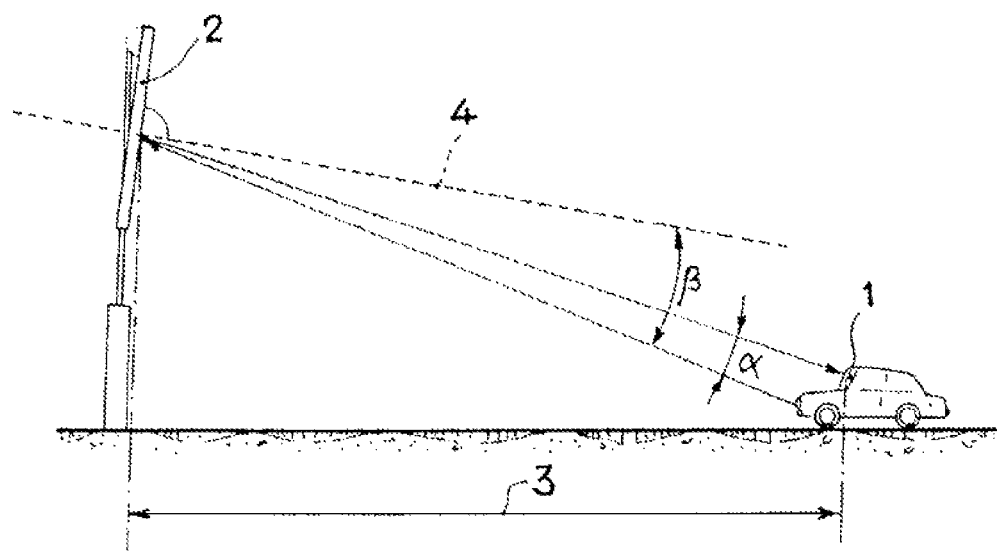
FIG. 1 shows a vehicle fitted with the device of the invention, approaching a traffic sign.

As can be seen in FIG. 1, a driver (1), as he goes along the road, perceives the information shown in the different signing elements. For a sign panel (2) lying within the angle of vision of the driver (1), at a distance (3) and in a defined instant, an angle of entrance β is defined formed between the light beam incident on the luminous surface at a point and normal (4) to that surface at that point, and also an angle of observation α formed by the light beam incident on the surface and the reflected light reaching the eyes of the driver (1). As the driver approaches the sign these angles change and the luminance perceived by the observer varies.

The luminance provided by a sign, especially if it consists of a back-reflecting material, depends on various factors:

Contributed light. In case of internally lit signs, the reflected light is independent of the contributed light, but for back-reflecting materials, the greater the amount of light that is contributed to the sign, the more light that is reflected.

Angle of entrance β and of observation α.

Special properties of the material. In particular the variation in back-reflection with the angle of visualization with respect to the normal.

The rotation of the sign about its axes (angles of twist, roll and dip).

In order to calculate the distance of the vehicle from the sign, a technique will be used based on the analysis of the images, using a single camera, though it can be extended to an array of cameras or specific techniques of triangulation or stereovision can be used. The procedure used in the present embodiment starts from the analysis of the image by known techniques of artificial vision which permits the position of an object of interest to be determined on that image on the basis of the size of that object as it appears in the image. Applied to different images of the same object, whose cadence is known thanks to the synchronism system, it is possible to establish a direct relation between the real size of the sign, the size of the sign in the image and the distance to the sign. Taking samples of the sizes of the object in the image, as well as the relative distances of the different images to one chosen as reference, it is possible to generate a set of geometric transformation equations on the basis of which the distance that is sought and the size of the object can be determined.

In order to carry out the procedure of the invention for determination of the luminance, a device is used which, fitted to a vehicle, comprises at least:

One camera for capturing the images.
A base illumination device.
An additional illumination device.
A positioning system.
A system for image and data recording and treatment.
A synchronism system.

Cameras

The aim of the present invention is to study the luminance perceived by the driver. For this reason, the location has been considered of at least one of the cameras in a suitable position on the vehicle that is close to the eye of the driver.

Digital cameras permit the colour coordinates of objects to be represented in an image defined by a set of pixels.

The representation of the colour is normally done by means of the coordinates R, G, B (Red, Green, Blue) though there exist other systems, for example in 1931 the International Commission on Illumination established the system XYZ or CIE 1931. In it, the Y component represents the energy or luminance of the pixel and X and Z the colour. For standard camera systems (PAL, NTSC) many different combinations have been defined for transforming the RGB system to XYZ, as in the case of standard ITU.BT-601. In this way, in order to obtain the luminance of an object, it will suffice to carry out the transformation between the systems and determine the value of Y.

In the system used in this embodiment, and depending on the camera, a conversion will be applied like that described above (standard) or a non-standard transformation that comprises the following steps:

A standard illuminant is selected defined by the CIE.

A white balance is carried out (see document "Digital Color Imaging Handbook", Gaurav Sharma, ed. CRC PRESS, Boca Raton, N.Y., Washington, D.C.).

Using a colour card according to the CIE 1931 standard, obtain the colour coordinates of pure red, green and blue with the camera.

Using a colour card, obtain the XYZ colour coordinates of pure red, green and blue with a colorimeter as per standard CIE 1931.

Obtain the conversion coefficients for colour to grey level starting from both measurements.

Figure 2:
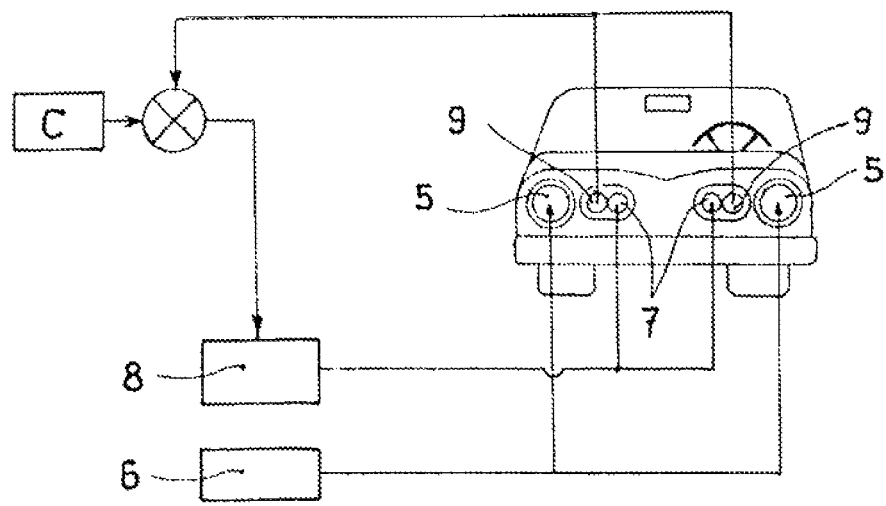
FIG. 2 shows the front of the above vehicle with the additional and base illumination devices.

The vehicle has two illumination systems, one which corresponds to the base illumination and the other which corresponds to the additional illumination. These two systems have to be adapted in order to permit a reliable measurement. See FIG. 2.

Base Illumination Device

In a preferred embodiment the base illumination (5) consists of the dipped lights of the vehicle, powered by the battery, whose voltage oscillates depending on its state of charge, its degree of aging, etc. Given that the illumination provided by these lights is directly related to the battery voltage, a stabilizer (6) needs to be inserted to compensate for the oscillations in that voltage.

Additional Illumination Device

In a preferred embodiment, the additional illumination (7) consists of the lamps external to the vehicle, which have to meet the following requisites:

They must provide a constant level of illumination during the data gathering, independently of oscillations in the supply voltage, of the temperature of the bulbs of the external lamps, and of the wear undergone by those lamps with time.

They have to provide a known level of illumination at each moment.

The level of illumination has to be able to be adjustable for each specific period of data gathering.

On account of all this, an adjustment control system (8) is needed for the additional illumination in a closed loop that can take on these responsibilities. Basically, the functioning of this system can be summarized as:

It measures the illumination by means of a sensor (9).

It compares it with a desired level C, modifiable by the operator.

It takes the decisions in the various control elements.

The map of intensity of the light provided by the additional lamps is known and controlled. Their light intensity is adjusted in such a way that avoids disturbing other circulating vehicles, preventing dangerous situations from arising that can be created by the other patents commented on above.

The additional lamps have to have a short response time. This can be achieved by means of lamps that are sufficiently fast (for example, based on LEDs) or with mechanical shutter systems that permit a sudden and controlled variation in the illumination that its provided.

The level of intensity of the illumination provided by the lamps has to be controlled and its geometric distribution has to be known.

The system described in the present embodiment permits data gathering to be done in movement along the road. In order to avoid disturbing other users travelling on the same road, it is necessary to follow the instructions regarding the design of lamps and maximum illumination levels for each emitter-observer angle that can be admissible, such as for example those defined in Regulation No 8 of the United Nations Economic Commission for Europe.

Image and Data Recording and Treatment System
The system comprises:
A digital storage device.
A device that applies some transformation equations enabling the luminance of each pixel to be obtained starting from its characteristic values (grey scale).

Positioning System
The system comprises:
A geo-referenced positioning device (GPS) and its corresponding antenna.
An information recording device.

Synchronism System
The system comprises a local positioning device (via the vehicle's milometer) which provides the distance traveled, and a device that generates certain events as a function of that distance traveled. The synchronism system allows adjustment of the distance from the start to when the images are captured and the delay time between each of them.

The synchronism system has to be such that permits adjustment of the on and off times of the lamps with sufficient precision for eliminating the subcyclic effects of public lighting. If f is the frequency of the grid (normally 50 Hz in Europe) the subcyclic effects have a duration of $1/(2*n*f)$ n=1 . . . N. On the other hand, given that the described device is capable of capturing images while moving, the duration of the time for capturing each image will be sufficiently small so as not to alter the size of the objects appearing in them and it will also be a multiple of the subcyclic frequencies. The interval of time between capturing two successive images of the same sign with variation in the illumination will be;

$$\Delta t = p/(2*n*f) \text{ with } n=1 \ldots N \text{ and } p=1 \ldots P.$$

In this way, as "n" and "p" are whole numbers, the moment of capturing each image will occur at the same point of the wave of the supply voltage from the electric grid, thus minimizing the differences in the uncontrolled ambient illumination.

The general operating procedure is as follows. A vehicle fitted with the devices and systems described above can circulate on the road and record different sequences of images of various signs situated along that road. With a view to a better understanding vertical signs will, for example, be used, though the procedure of the present invention is valid for any kind of sign that is the object of study.

As the vehicle approaches the sign (11), the sign will be seen to become displaced in the image and its size will increase until it disappears from the field visible to the camera.

The method that allows the effects of external illumination, such as public lighting (10) for example, to be cancelled out consists of capturing images with different illumination levels, by a combination of base illumination (5) and the additional illumination (7) of the vehicle, obtaining the value of the differential luminance, which cancels out the effect of the ambient illumination as well as the base illumination of the vehicle.

Figure 3:
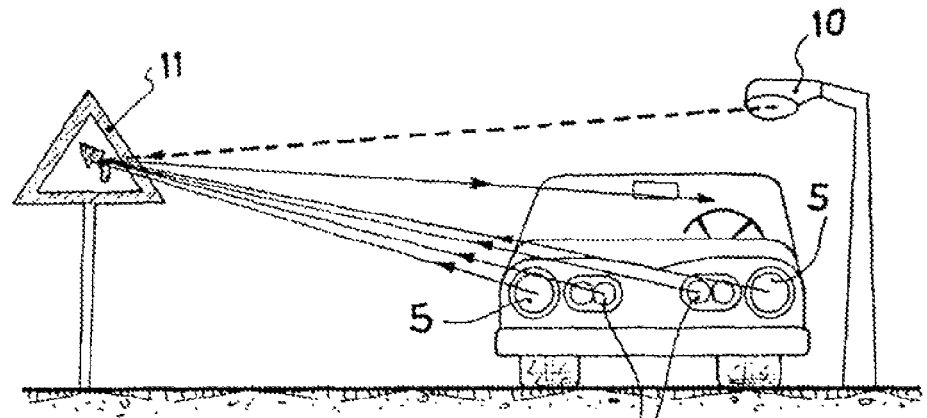
Figure 4:
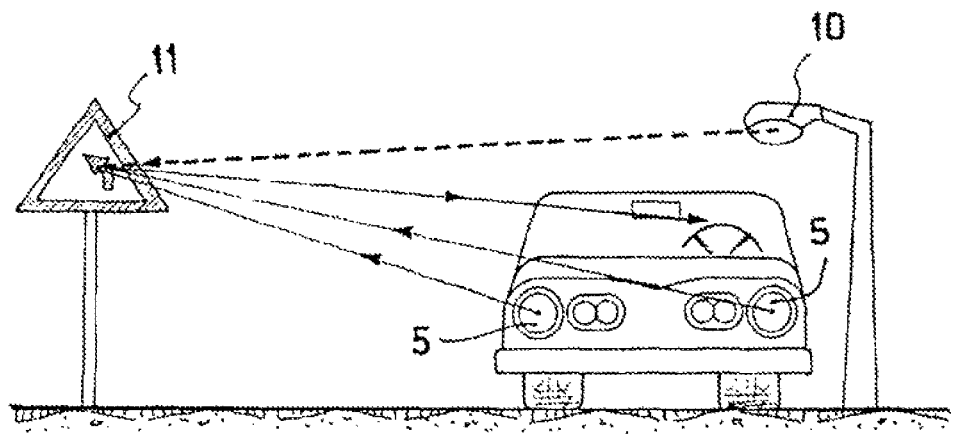

As can be seen in FIG. 3, first of all the images are captured with the base illumination (5) and the additional illumination (7) switched on. Then, with an interval of time determined by the synchronism device, the additional illumination (7) is switched off or hidden in order to obtain the second image as can be seen in FIG. 4.

Figure 5:
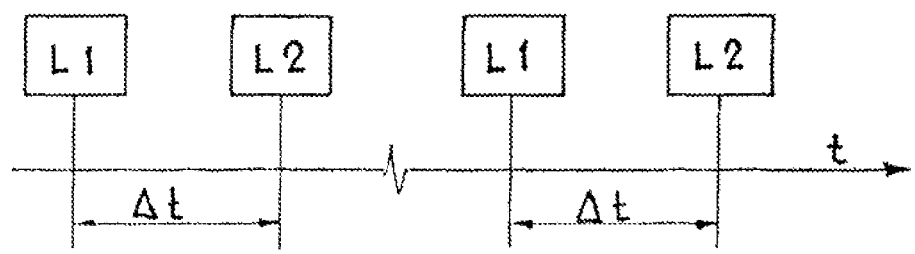
FIG. 5 shows, schematically in time, the determination of the luminance of two traffic signs.

The synchronism system establishes the instants of time in which the two images are captured corresponding to two illumination levels L1 and L2. See FIG. 5.

Finally, the location data is stored, along with the time of the synchronism system.

Once the data has been downloaded, an automatic computer programme processes the images where the vertical signs (11) appear and it extracts the region corresponding to that sign. Another automatic procedure calculates the luminance level on the basis of a grey scale. Finally, the differential luminance is obtained from L1 and L2.

The relation with the positioning system allows the relative position of the image and the sign on the road to be calculated.

It will be evident to an expert in the subject that, without departing from the essence of the invention, there is a series of modifications and variants that can be made allowing it to be adapted to the desired operating conditions. So, the additional illumination system has been described as an external light incorporated into the vehicle, but it could be included among the vehicle's own lamps with suitable control. No details have been given of those processes and devices which, being conventional, will be more than familiar to the expert in the subject.

The invention claimed is:
1. A determination procedure of luminance of traffic signs comprising the following stages:
a) obtaining a sequence of images at a frequency corresponding to a frequency of an electric grid such that the sequence of images are obtained at an identical point of a sine wave that characterizes an electric grid supply voltage, the sequence of images including a first image with a first illumination level and a second image with a second illumination level, the firsst illumination level corresponding to a stabilized base illumination and the second illumination level corresponding to the stabilized base illumination and an additional illumination, the sequence of images being obtained at a frequency of an electric grid such that the first and second images are obtained at an identical point of a sine wave characterizing a supply voltage from the electric grid;
b) extracting a first region of the image corresponding to a sign represented in the image and extracting a second region of the second image, the second region corresponding to the sign represented in the second image;
c) calculating a first luminance value of the sign using the first region, the first luminance value being the sum of luminance due to the stabilized base illumination $L_a$, luminance due to the additional illumination $L_b$ and luminance due to uncontrolled ambient illumination $L_c$, whereby the first luminance value L1 is

$$L1 = L_a + L_b + L_c,$$

d) calculating a second luminance value of the sign using the second region, the second luminance value being the sum of luminance due to the stabilized base illumination $L_a$ and luminance due to the ambient illumination $L_d$, the second luminance value L2 is:

$$L2 = L_a + L_d,$$

e) obtaining a luminance difference value of the sign corresponding to the first luminance value and the second luminance value L2, wherein, the luminance difference value ΔL obtained is the luminance corresponding to the additional illumination L$b$, $$\Delta L = L1 - L2 = L_b,$$

such that, the effect of the ambient illumination and the stabilized base illumination have been suppressed.

2. The determination procedure of the luminance of traffic signs in accordance with claim 1, wherein the obtaining of the two images with different illumination levels is done with an interval of time equal to $\Delta t = p/(2*n*f)$ where "f" is the supply frequency of the public lighting network and "n" and "p" are whole numbers.

3. A device for determination of luminance of traffic signs, using the procedure according to claim 1, the device coupled to a vehicle, the device comprising: at least one camera for capturing the images, a stabilized base illumination device, an additional illumination device, a positioning system, a system for image and data recording and treatment, a synchronism system for the picking up of two images with different illumination levels.

4. The device for the determination of the luminance of traffic signs in accordance with claim 3, wherein one of the at least one camera for obtaining images is a digital camera.

5. The device for the determination of the luminance of traffic signs in accordance with claim 3, wherein the base illumination device comprises the dipped lights of the vehicle with a stabilizer system.

6. The device for the determination of the luminance of traffic signs in accordance with claim 3, wherein the additional illumination device comprises external lamps and an adjustment and control device that includes sensors for measuring the light intensity of the external lamps to maintain a constant illumination level modifiable by an operator.

7. The determination procedure of the luminance of traffic signs in accordance with claim 1, wherein the luminance difference value ΔL is in units of candelas per area.

8. The determination procedure of the luminance of traffic signs in accordance with claim 1, wherein the first and second images are converted to the first luminance value L1 and the second luminance value L2, respectively, using a change equation, and wherein the change equation is determined based on values provided from a luminance meter.

9. The determination procedure of the luminance of traffic signs in accordance with claim 1, wherein the first region of the first image corresponds to an array of pixels in the first image and the second region of the second image corresponds to an array of pixels in the second image.

* * * * *